United States Patent [19]

Smith

[11] Patent Number: 4,803,267

[45] Date of Patent: Feb. 7, 1989

[54] PROCESS FOR PREPARING CEPHALOSPORIN COMPOUNDS

[75] Inventor: Gordon C. D. Smith, Wokingham, England

[73] Assignee: Glaxo Group Limited, London, England

[21] Appl. No.: 771,009

[22] Filed: Aug. 30, 1985

Related U.S. Application Data

[62] Division of Ser. No. 399,328, Jul. 19, 1982, Pat. No. 4,563,523.

[30] Foreign Application Priority Data

Jul. 17, 1981 [GB] United Kingdom ................. 8122147

[51] Int. Cl.$^4$ ............................................. C07D 501/18
[52] U.S. Cl. ..................................... 540/224; 540/225
[58] Field of Search .................. 544/25; 540/224, 225, 540/221

[56] References Cited

U.S. PATENT DOCUMENTS

| | | | |
|---|---|---|---|
| 3,207,755 | 9/1965 | Abraham et al. | 260/243 |
| 3,261,832 | 7/1966 | Cowley | 260/243 |
| 3,270,009 | 8/1966 | Flynn | 544/25 |
| 3,449,338 | 1/1970 | Flynn | 260/243 |
| 3,498,979 | 3/1970 | Crisp | 260/243 |
| 3,792,047 | 2/1974 | Arkley et al. | 260/243 C |
| 3,882,108 | 5/1975 | Chapman et al. | 260/243 C |
| 4,021,426 | 5/1977 | Oppici et al. | 260/243 C |
| 4,245,088 | 1/1981 | Tsushima et al. | 544/16 |
| 4,332,798 | 6/1982 | Teraji et al. | 424/246 |
| 4,369,313 | 1/1983 | Jones et al. | 544/24 |

*Primary Examiner*—Nicholas S. Rizzo
*Attorney, Agent, or Firm*—Bacon & Thomas

[57] ABSTRACT

The invention relates to the novel compound (6R,7R)-7-(D-5-benzamido-5-carboxypentanamido)-3-(1-pyridiniummethyl)-ceph-3-em-4-carboxylate and salts thereof, which may be prepared in substantially pure form. The novel compounds are useful for the preparation of (6R,7R)-7-amino-3-(1-pyridiniummethyl)ceph-3-em-4-carboxylate or salts thereof, which are themselves useful for the preparation of 7-substituted 3-pyridiniummethyl cephalosporin antibiotics such as ceftazidime and cephaloridine.

3 Claims, No Drawings

PROCESS FOR PREPARING CEPHALOSPORIN COMPOUNDS

This application is a division of application Ser. No. 399,328, filed on Jul. 19, 1982, now U.S. Pat. No. 4,563,523.

This invention relates to novel cephalosporin compounds and their use in the preparation of cephalosporin compounds having pharmacological activity.

The cephalosporin compounds in this Specification are named with reference to "cepham" after J. Amer. Chem. Soc. 1962, 84, 3400, the term "cephem" referring to the basic cepham structure with one double bond.

Cephalosporin antibiotics are widely used in the treatment of diseases caused by pathogenic bacteria in human beings and animals. Various cephalosporin compounds which exhibit valuable pharmacological properties include certain compounds having a pyridiniummethyl substituent at the 3-position of the cephalosporin nucleus, and particular substituents at the 7-position of the nucleus.

Thus, for example, U.K. Patent Specification No. 2025398A describes cephalosporin antibiotics of the general formula

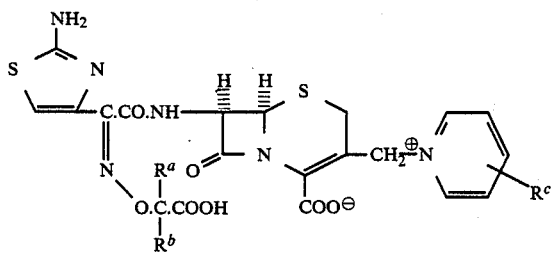

(wherein $R^a$ and $R^b$, which may be the same or different each represents a $C_{1-4}$ alkyl group or $R^a$ and $R^b$ together with the carbon atom to which they are attached form a $C_{3-7}$ cycloalkylidene group; and $R^c$ represents hydrogen or a 3- or 4-carbamoyl group) and salts and esters thereof.

A particularly advantageous compound of the above formula is (6R,7R)-7-[(Z)-2-(2-aminothiazol-4-yl)-2-(2-carboxyprop-2-oxyimino)acetamido]-3-(1- pyridiniummethyl)ceph-3-em-4-carboxylate, which has been given the approved name, 'ceftazidime'.

A further 3-pyridiniummethyl cephalosporin having pharmaceutical importance is (6R,7R)-7-[2-(thien-2-yl)acetamido]-3-(1-pyridiniummethyl)ceph-3-em-4-carboxylate, having the approved name 'cephaloridine'.

Other 3-pyridiniummethyl cephalosporins are described, for example, in European Patent Application Specifications Nos. 27599, 45937 and 46964.

A convenient starting material for the preparation of such cephalosporin antibiotics is (6R,7R)-7-amino-3-(1-pyridiniummethyl)ceph-3-em-4-carboxylate or a salt thereof. We have found the dihydrochloride salt to be a particularly advantageous starting material.

In general, the basic starting material in an overall process for the preparation of pharmacologically useful cephalosporin compounds is cephalosporin C, i.e. (6R,7R)-7-[D-5-amino-5-carboxypentanamido]-3-(acetoxymethyl)ceph-3-em-4-carboxylic acid and salts thereof, such as its sodium, potassium or zinc salt, or desacetyl cephalosporin C, that is the 3-hydroxymethyl analogue of cephalosporin C, and its salts. These starting materials may be modified at both the 7- and 3-positions of the cephalosporin molecule. At some stage during the overall process the original 7-side chain is generally removed to give a 7-amino cephalosporin.

A number of methods for the preparation of 7amino cephalosporins from cephalosporin C or a derivative thereof have previously been described in the art.

Thus, for example British Patent Specification No. 1391437 describes a process for the preparation of 7-amino cephalosporins by reacting a 7-acylaminocephalosporin with a phosphorus trihalide in an anhydrous inert organic solvent, contacting the resulting solution with an imide halide forming compound, commingling the reaction mixture with an imino-ether forming compound and recovering the desired 7-amino cephalosporin. The starting material employed in this process may be a compound of formula

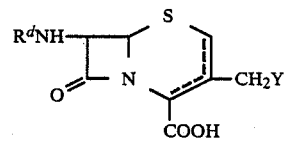

(wherein $R^d$ is a carboxylic acyl group e.g. a 5-aminoadipoyl group or a derivative thereof; Y is hydrogen, acetoxy or the residue of a nucleophile; and the dotted line indicates that the compound can be a ceph-2-em or ceph-3-em compound) or a salt thereof.

British Patent Specification No. 1467355 describes a process for the preparation of 6-aminopenicillanic acid and derivatives at the 3-position of 7-aminocephalosporanic acid by reacting a corresponding 6- or 7-acylamino penicillin or cephalosporin respectively with a molar excess of an oxalyl halide, treating the product with a halogenating agent and simultaneously or subsequently with an alkyl orthoformate or primary or secondary alcohol, and then hydrolysing the obtained iminoether with a mixture of water and an alkanol. Starting materials which may be used in the process include 7-acylamino cephalosporins of the formula

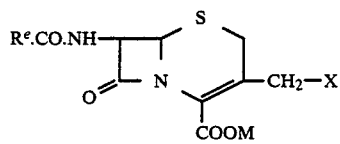

Among the large number of radicals mentioned for $R^e$, M and X in this formula, there are included compounds in which $R^e$ is a group of formula

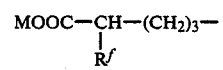

(in which M is as defined below, and $R^f$ is inter alia an amino or a protected amino group); M is hydrogen or a metal or ammonium cation; and X is inter alia a pyridinium group.

Neither British Patent Specification No. 1391437 nor British Patent Specification No. 1467355 specifically discloses the preparation of 7-amino-3-pyridiniummethylcephalosporins.

British Patent Specification No. 2052490A describes the preparation of (6R,7R)-7-amino-3-(1-pyridiniummethyl)ceph-3-em-4-carboxylate dihydrochloride by deacylation of corresponding 7-acylamino compounds, where the acyl group may for example be a 5-aminoadipoyl group which may have one or both of the carboxyl and amino groups blocked. The preparation of the 7-amino compound starting from cephaloridine is exemplified. As cephaloridine itself is prepared in several stages from cephalosporin C, this overall process is quite lengthy.

European Patent Application Specification No. 27599 describes the preparation of (6R,7R)-7-amino-3-(1-pyridiniummethyl)ceph-3-em-4-carboxylate dihydrochloride dihydrate from (6R,7R)-7-[D-5-carboxy-5-(3-phenylureido)-pentanamido)-3-(1-pyridiniummethyl)ceph-3-em-4-carboxylate, the latter compound having been prepared by reacting sodium (6R,7R)-7-[D-5-carboxy-5-(3-phenylureido)pentanamido)-3-acetoxymethylceph-3-em-4-carboxylate with pyridine. The overall yield is, however, relatively low.

Thus, previous processes for the preparation of (6R,7R)-7-amino-3-(1-pyridiniummethyl)ceph-3-em-4-carboxylate from a basic starting material of cephalosporin C or its derivatives have not been particularly efficient. There is no disclosure in the art of an intermediate which may readily be derived from cephalosporin C or desacetyl cephalosporin C and which may be efficiently converted into a 7-amino-3-pyridiniummethyl cephalosporin.

We have now discovered a novel cephalosporin compound and its salts, which may be used in a short, economical and convenient process for the preparation of 7-amino-3-pyridiniummethyl cephalosporins.

According to one aspect of the present invention there is provided the compound of formula

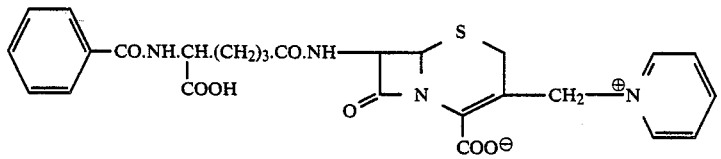

(I)

and salts thereof. Salt derivatives may include inorganic base salts, such as alkali metal salts (e.g. sodium or potassium salts) and alkaline earth metal salts (e.g. calcium salts); organic base salts (e.g. procaine, phenylethylbenzylamine, dibenzylethylenediamine, ethanolamine, diethanolamine and N-methylglucosamine salts); and acid addition salts (formed with, for example, a mineral acid such as hydrochloric, hydrobromic, sulphuric, nitric or phosphoric acid or an organic acid such as trifluoroacetic acid, methanesulphonic or toluene-p-sulphonic acid).

The compounds of the invention may readily be prepared in a substantially pure form, and in high yield.

The compounds of the invention may advantageously be used to prepare the compound (6R,7R)-7-amino-3-(1-pyridiniummethyl)ceph-3-em-4-carboxylate or a salt thereof, e.g. the dihydrochloride salt, which is obtained crystalline, substantially pure and in high yield. As described above, this compound is a particularly advantageous intermediate for the preparation of 7-substituted-3-pyridiniummethyl cephalosporin antibiotics such as ceftazidime and cephaloridine.

Furthermore, we have found that the compound of formula (I) may readily be obtained crystalline, which is a preferred embodiment of the invention. The crystalline material is obtained in high yield and has good stability.

The crystalline compound of formula (I) has been characterised by its X-ray powder diffraction pattern. X-Ray crystallographic data in respect of this compound are given in the following Table.

All 'd' values are given in Ångstrom units and were taken from the CoK$_\alpha$ exposure for the higher 'd' spacings and the CuK$_\alpha$ exposure for the lower ($<3$Å) 'd' spacings.

TABLE

| d (Å) | Intensity | d (Å) | Intensity |
|---|---|---|---|
| 15.09 | m | 3.70 | vw |
| 8.55 | wd | 3.52 | vw |
| 7.87 | w | 3.24 | w |
| 6.35 | m | 3.09 | wd |
| 5.36 | vw | 2.98 | wd |
| 5.14 | vw | 2.87 | vwd |
| 5.03 | vw | 2.72 | w |
| 4.80 | s | 2.63 | w |
| 4.65 | s | 2.49 | vw |
| 4.49 | w | 2.42 | vwd |
| 4.26 | m | 2.30 | 2 vw |
| 4.17 | m | 2.15 | 2 vw |
| 4.07 | vs | 2.11 | 2 vw |
| 3.99 | vs | 2.07 | 2 vw |
| 3.82 | vw | 2.03 | 2 vw | s = strong  m = medium  w = weak  v = very  d = diffuse.

Compounds of the invention may be prepared by either of the following processes, which themselves form further features of the invention:

(A) by reacting a compound of formula

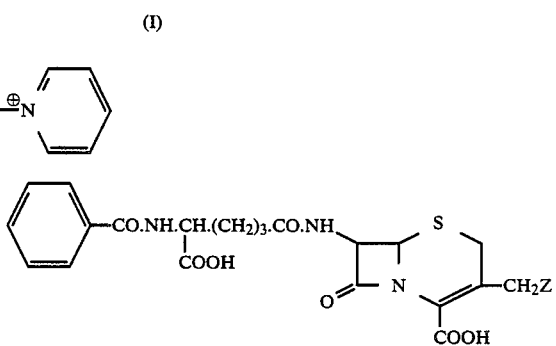

(II)

(wherein Z is a replaceable residue of a nucleophile e.g. an iodine atom or an acyloxy group such as an acetoxy or dichloroacetoxy group) or a salt, e.g. a disodium salt, or protected derivative thereof, with pyridine, followed, where necessary, by removal of any protecting groups; and (B) by N-benzoylating the compound of formula

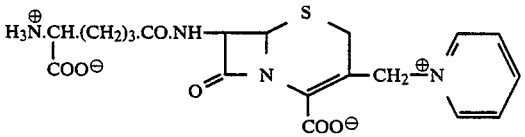

(III)

or a salt thereof.

We have found that the compound of formula (I) may be obtained crystalline by adjusting the pH of an aqueous solution of a salt of the compound of formula (I) using e.g. phosphoric acid, to between 2.0 and 5.0 and isolating the desired product. The salt may for example be an alkali metal salt. The compound of formula (I) or its salts may conveniently be obtained crystalline after treatment of the solvent medium containing the crude compound with an ion-exchange resin, preferably a liquid ion exchange resin such as Amberlite LA-2 (a weakly basic high molecular weight secondary amine). Other suitable ion exchange resins include weakly basic liquid or solid polyamine resins and strongly basic liquid or solid quaternary ammonium resins such as Amberlite LA-1, Amberlite IRA 93, Aliquat 336 and A101D. Amberlite resins are sold by Rohm and Haas, Philadelphia, USA; A101D. by Duolite International Limited, Middlesex, England; and Aliquat 336 by General Mills Chemicals Inc. Minneapolis, Minnesota.

The compound of formula (III) may be prepared, for example, by reaction of pyridine with a compound of formula (IV)

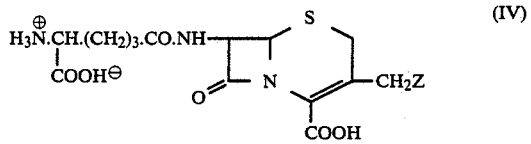

(wherein Z is as defined above) or a salt or protected derivative thereof, followed, where necessary, by the removal of any protecting groups.

Where Z in a compound of formula (II) or (IV) is iodine, the compound may be prepared by reaction of a compound of formula (V)

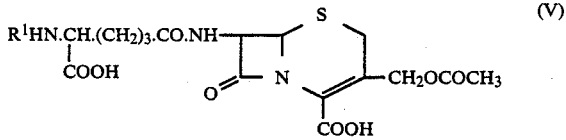

(wherein $R^1$ is hydrogen or benzoyl) or a salt, zwitterion or protected derivative thereof, with a trialkyliodosilane, followed, where necessary by removal of any protecting groups. The alkyl groups of the trialkyliodosilane preferably contain 1-6 carbon atoms, for example trimethyliodosilane. The iodination reaction may conveniently be carried out as described in U.S. Pat. No. 4266049.

Compounds of formula (II) or (IV) where Z represents an acyloxy group may be prepared by acylation of a compound of formula

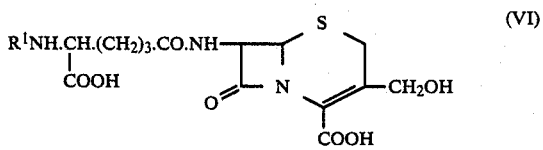

(wherein $R^1$ is as defined above) or a salt, zwitterion or protected derivative thereof, followed, where necessary, by removal of any protecting groups. The acylation reaction may be carried out for example as described in British Patent Specification No. 1,141,293. The compound of formula (VI), wherein $R^1$ represents hydrogen, may be obtained by fermentation e.g. as described in British Patent Specification No. 1,433,528 or 2060610A.

As indicated above, the compounds according to the invention may advantageously be used in a process for the preparation of 7-amino-3-pyridiniummethylcephalosporins.

Thus, in another aspect, the invention provides a process for the preparation of the compound of formula

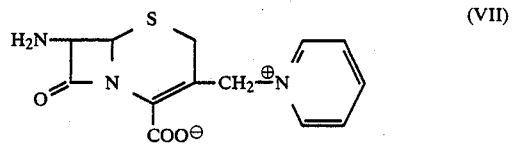

or a salt thereof, e.g. an acid addition salt (formed with, for example, any one of the above mentioned mineral or organic acids); which process includes the step of removing the 7-side chain of a compound of formula (I).

The preparation of the compound of formula (VII) from the compound of formula (I) will generally form part of an overall reaction process, conveniently starting from cephalosporin C, its desacetyl analogue or a derivative thereof.

Thus, in a still further aspect, the invention provides a process for the preparation of the compound of formula (VII) as defined above, or a salt thereof, which process comprises removing the 7-side chain of the compound of formula (I) or a salt thereof, said compound having been prepared by any one of the following processes:

(a) N-benzoylating cephalosporin C or a salt thereof to form the compound of the formula (II) (wherein Z is acetoxy) or a salt thereof and reaction thereof with pyridine to form the compound of formula (I) or a salt thereof;

(b) N-benzoylating cephalosporin C or a salt thereof, reaction of the product so formed or a protected derivative thereof with a trialkyliodosilane to form a compound of formula (II) (wherein Z is an iodine atom) or a salt or protected derivative thereof, followed by reaction thereof with pyridine and, where necessary, removal of any protecting groups to form the compound of formula (I) or a salt thereof;

(c) N-benzoylating desacetyl cephalosporin C or a salt thereof to form the compound of formula (VI) (wherein $R^1$ is benzoyl) or a salt thereof and reacting this compound or a protected derivative thereof with an acylating agent, to form a compound (II) (wherein Z is an acyloxy group) or a salt or protected derivative thereof followed by reaction with pyridine and, where necessary, removal of any protecting groups to form the compound of formula (I) or a salt thereof;

(d) reacting cephalosporin C or a salt thereof with pyridine to form a compound of formula (III) as defined above or a salt thereof, followed by benzoylation thereof to form the compound of formula (I) or a salt thereof;

(e) reacting cephalosporin C or a salt or protected derivative thereof with a trialkyliodosilane to form a compound of the formula (IV) (wherein Z is an iodine atom) or a salt or protected derivative thereof, followed by reaction with pyridine, and where necessary, removal of any protecting groups to form a compound of formula (III) or a salt thereof, which is N-benzoylated to form the compound of formula (I) or a salt thereof; and (f) reacting desacetyl cephalosporin C or a salt or protected derivative thereof with an acylating agent, followed, where necessary, by removal of protecting groups to form a compound of formula (IV) (wherein Z is an acyloxy group) or a salt thereof which compound is either (i) reacted with pyridine to form the compound of formula (III) as defined above or a salt thereof, followed by N-benzoylation to form the compound of formula (I) or a salt thereof; or (ii) N-benzoylated to form a compound of formula (II) as defined above or a salt thereof, followed by reaction with pyridine to form a compound of formula (I) or a salt thereof.

If desired, the compound of formula (VII) prepared by the above processes is converted to an acid addition salt thereof.

A preferred salt of the compound of formula (VII) produced by the above processes is the dihydrochloride salt, especially the dihydrochloride salt in the form of a dihydrate.

The benzoylation reaction according to the above described processes is preferably effected using benzoyl chloride. The reaction medium is conveniently an aqueous organic solvent, for example, an aqueous ketone such as aqueous acetone, or an aqueous alkanol such as a lower alcohol or mixture of alcohols e.g. aqueous industrial methylated spirits. The pH of the reaction medium is conveniently in the range 7 to 10, preferably 8 to 9.

The displacement of Z by pyridine according to the above described processes may conveniently be effected by maintaining the reactants in solution or suspension, advantageously using from 1 to 10 moles of pyridine.

Nucleophilic displacement reactions may be carried out on those compounds wherein the 3-methyl substituent is an acyloxy group or an iodine atom for example as discussed below.

Displacement reactions on compounds where the 3-methyl substituent is an acyloxy group, particularly an acetoxy group, may be facilitated by the presence in the reaction medium of iodide or thiocyanate ions. Reactions of this type are described in more detail in British Patent Specifications Nos. 1132621 and 1171603. The reaction is advantageously effected in an aqueous medium, preferably at a pH of 5 to 8, particularly 5.5 to 7, and at a temperature of 30° to 110° C., preferably 50° to 80° C.

The above-described processes employing compounds in which Z is the residue of a substituted acetic acid may be carried out as described in British Patent Specification No. 1241657.

When the nucleophilic displacement reaction is carried out on compounds where Z is an acyloxy group, the carboxyl groups of the cephalosporin are preferably not protected.

The reaction of pyridine with compounds in which the 3-methyl substituent is an iodine atom is conveniently effected in a non-aqueous medium which preferably comprises one or more organic solvents, advantageously of a polar nature, such as ethers e.g. dioxan or tetrahydrofuran, esters e.g. ethyl acetate, amides e.g. formamide and N,N-dimethylformamide, and/or ketones e.g. acetone. In certain cases pyridine itself may be the solvent. The reaction medium should be neither extremely acidic nor extremely basic. The nucleophilic displacement reaction with pyridine is conveniently effected at a temperature of $-10°$ to $+50°$ C., preferably $+10°$ to $+30°$ C.

The compounds where Z is an iodine atom are preferably prepared and used in subsequent reactions in protected form. They are conveniently not isolated prior to the reaction with pyridine.

The protecting groups may be any of the conventional protecting groups known in the art for example as described in British Patent Specification No. 1399086. However, trialkylsilyl groups, such as trimethylsilyl, are preferred. These may be formed with for example a trialkylchlorosilane, e.g. trimethylchlorosilane.

The removal of the 7-side chain from the compound of formula (I) or a salt thereof according to the above processes may conveniently be effected by contacting the compound with phosphorus pentachloride, converting the imide chloride so formed into an imino ether and hydrolysing or alcoholysing the imino ether to yield the desired compound. It is generally necessary in such reactions to protect the 4-carboxyl group by a group which may readily be split off as and when desired. This may conveniently be effected by silylation of the 4-carboxyl group. Such a deacylation process is described in, for example, British Patent Specification Nos. 1241655 and 2052490A.

Base salts of the compound of formula (I) may be formed by reacting a corresponding acid with the appropriate base. Thus, for example, sodium or potassium salts may be prepared using the respective 2-ethylhexanoate or hydrogen carbonate salt.

Acid addition salts may be prepared by reacting a compound of formula (I) or (VII) with the appropriate acid.

As indicated above a preferred acid addition salt of the compound of formula (VII) is the dihydrochloride, which may be prepared as the dihydrate. This may be effected by contacting the reaction mixture with water or an aqueous medium or, if necessary, an aqueous solution of hydrogen chloride, or by dissolving the dihydrochloride in aqueous hydrochloric acid and thereafter precipitating the dihydrochloride dihydrate therefrom by addition of a suitable reagent e.g. a lower alkanol such as isopropyl alcohol.

The following Examples serve to illustrate the invention. All temperatures are in °C.

Proton magnetic resonance (p.m.r.) spectra were determined at 100 MHz. The integrals are in agreement with the assignments; coupling constants, J, are in Hz, the signs not being determined; s=singlet, d=doublet, dd=double doublet, t=triplet, m=multiplet, and ABq=AB quartet.

H.p.l.c. is high performance liquid chromatography.

EXAMPLE 1

(6R,7R)-7-(D-5-Benzamido-5-carboxypentanamido)-3-acetoxymethylceph-3-em-4-carboxylic acid disodium salt Potassium (6R,7R)-7-(D-5-amino-5-carboxypentanamido)-3-acetoxymethylceph-3-em-4-carboxylate (90.8 g) was stirred in water (600 ml) at ambient temperature. The pH of the aqueous mixture was raised to 8.5 by the addition of 50% aqueous tri-potassium phosphate (6 ml). A solution of benzoyl chloride (25.4 ml) in acetone (400 ml) was added over 70 minutes and the pH of the reaction mixture was maintained at 8.3–8.5 by the addition of 50% aqueous tri-potassium phosphate (170 ml). The resulting solution was stirred for 45 minutes, diluted with water (500 ml) and ethyl acetate (500 ml) and the pH lowered to 5 with phosphoric acid. The two phases were separated, ethyl acetate (1l) was added to the aqueous layer and the pH lowered to 2 with phosphoric acid. The phases were separated and the aqueous layer re-extracted with ethyl acetate (500 ml). The combined ethyl acetate extracts were stirred with sodium sulphate for 30 minutes, filtered, and the cake washed with a little ethyl acetate. The filtrate and washings were evaporated down to an oil on a rotary evaporator at 40° and the residue dissolved in acetone (400 ml). Sodium 2-ethylhexanoate (66.5 g) was dissolved in acetone (300 ml) and after clarification, the solution of sodium 2-ethylhexanoate was added over 30 minutes to the stirred acetone solution of the title acid at ambient temperature. The resulting suspension was stirred for 15 minutes and the product was collected by vacuum filtration washed with acetone (500 ml) and dried overnight in vacuo at room temperature, to give the title compound (98.4 g); UV (pH 6 buffer) λmax 232 nm, $E_{1cm}^{1\%}$ 257; λinf 263 nm, $E_{1cm}^{1\%}$ 148.

EXAMPLE 2

(6R,7R)-7-[D-5-benzamido-5-carboxypentanamido]-3-(1-pyridiniummethyl)ceph-3-em-4-carboxylate Sodium iodide (102.5 g) and pyridine (8.5 ml) were mixed in water (20 ml) and the solution was heated to 60°. (6R,7R)-7-(D-5-Benzamido-5-carboxypentanamido)-3-acetoxymethylceph-3-em-4-carboxylic acid disodium salt (28.15 g) was added and washed in with water (5 ml). The solution was stirred at 60° for 3.25 hours, cooled and diluted with acetone (50 ml). The reaction mixture was added to stirred acetone (1.75 l) over 30 minutes; cooled to 0° and the crude product collected by vacuum filtration, washed with acetone (250 ml) and ether (150 ml) and dried overnight in vacuo at ambient temperature, giving the crude title compound (35.3 g).

43.5 g of the crude title compound, prepared similarly, was dissolved in water (195 ml) and stirred with Amberlite LA-2 (309 ml) in ether (570 ml) containing formic acid (21.3 ml) for 20 minutes. The layers were separated and the organic phase back extracted with water (30 ml). The combined aqueous extracts were washed with ether and concentrated to ca 124 g on a rotary evaporator at 40°.

A portion of the concentrate was stirred at room temperature and the pH lowered to 4.1 with phosphoric acid. The suspension was aged at 0° for 2 hours and the product collected by vacuum filtration, washed with cold water and acetone and dried in vacuo at 40° to give the crystalline title compound (5.3 g); $C_{26}H_{26}N_4SO_7 \cdot 0.588\ H_2O$ requires C, 56.86%; H, 4.99%; N, 10.2%; S, 5.84%; found C, 56.66%; H, 4.93%; N, 10.05%; S, 5.7%; h.p.l.c. purity 97.1%; $[\alpha]_D^{20} +29.2°$ (C 1.0, pH 6 buffer); $\lambda_{max}$ 236 nm $E_{1cm}^{1\%}$ 310, $\lambda_{inf}$ 252 nm, $E_{1cm}^{1\%}$ 297 (pH 6 buffer); water content by Karl Fischer method 1.9%. X-Ray data for the title compound are given in the Table above.

EXAMPLE 3

(6R,7R)-7-[D-5-benzamido-5-carboxypentanamido]-3-(1-pyridiniummethyl)ceph-3-em-4-carboxylate Potassium thiocyanate (22.5 g) and pyridine (3.4 ml) were stirred together in water (5 ml) and heated to 80°. (6R,7R)-7-(D-5-Benzamido-5-carboxypentanamido)-3-acetoxymethylceph-3-em-4carboxylic acid disodium salt (11.27 g) was added and the mixture was stirred at 80° for 40 minutes. The clear solution was cooled, diluted with acetone (50 ml) and poured into vigorously stirred acetone (500 ml). The resulting suspension was stirred at ambient temperature for 1 hour and the crude product collected by vacuum filtration. The bed was washed with acetone (50 ml) and a little diethyl ether and the product was dried overnight in vacuo at room temperature to give the title compound as powder (13.6 g).

This was dissolved in water (65 ml) and stirred with Amberlite LA-2 resin (103 ml) in diethyl ether (190 ml) containing formic acid (7.1 ml) for 20 minutes at ambient temperature. The phases were separated and the organic phase re-extracted with water (10 ml). The combined aqueous extractions were washed with diethyl ether (30 ml) and concentrated on a rotary evaporator at 50° (41 g). The pH of the aqueous solution was lowered to 2.9 by the addition of phosphoric acid and the suspension stirred for 15 minutes, before ageing at 5° for 3 hours. The product was collected by vacuum filtration, washed with ice-cold water (8 ml) and acetone (20 ml) and dried overnight in vacuo at 40° to give the title compound (5.81 g). U.V. λmax 234 nm $E_{1cm}^{1\%}$ 293 (pH 6 buffer); h.p.l.c. 97% pure.

EXAMPLE 4

(a)

(6R,7R)-7-(D-5-Benzamido-5-carboxypentanamido)-3-acetoxymethylceph-3-em-4-carboxylic acid disodium salt.

Potassium (6R,7R)-7-(D-5-amino-5-carboxypentanamido)-3-acetoxymethylceph-3-em-4-carboxylate (30.0 g) was stirred in water and cooled to 5°. The pH of the aqueous mixture was raised to 8.3–8.5 by the addition of 10% w/v aqueous sodium hydroxide. Benzoyl chloride (8.69 ml) was added over 4 minutes and the pH of the reaction mixture was maintained at 8.3–8.5 by the addition of 10% w/v aqueous sodium hydroxide. The reaction mixture was stirred for a further 1 hour with the addition of 10% w/v aqueous sodium hydroxide maintaining the pH at 8.3–8.5. Ethyl acetate (100 ml) was added to the resulting solution and the pH lowered to 5 with 15% v/v sulphuric acid. The two phases were separated, ethyl acetate (265 ml) and acetone (53 ml) were added to the aqueous layer and the pH lowered to 2.2 with 15% v/v sulphuric acid. The phases were separated and the aqueous layer reextracted with ethyl acetate (80 ml). The combined ethyl acetate extracts were washed with water (80 ml). The two phases were separated. The ethyl acetate phase was stirred with sodium sulphate (20 g) for 10 minutes, filtered and the cake washed with a little ethyl acetate. The filtrate and washings were evaporated to a foam on a rotary evaporator and the residue dissolved in industrial methylated spirits (IMS) (150 ml). To this stirred solution was added sodium 2-ethylhexanoate (22.0 g) dissolved in IMS (100 ml) over 30 minutes at 12°. The resulting suspension was stirred for 15 minutes at 12° and the product was collected by vacuum filtration, washed with IMS (165 ml) chilled at 5° and dried overnight in vacuo at 40° to give the title compound (29.81 g). The U.V. spectrum resembled that of the product of Example 1

(b)

(6R,7R)-7-(D-5-Benzamido-5-carboxypentanamido)-3-(1-pyridiniummethyl)ceph-3-em-4 carboxylate.

Potassium thiocyanate (38.1 g) was dissolved in water (8.25 ml) by heating to 70°, with stirring. When a complete solution had formed, pyridine (5.75 ml) was added followed by the product of stage (a) (19.05 g). The mixture was stirred for 2 hours at 70°. The resulting solution was cooled to 60°, diluted with acetone (90 ml) and added over 40 minutes to stirred acetone (840 ml). The resulting suspension was stirred at ambient temperature for 30 minutes and the crude product was recovered by vacuum filtration. The bed was washed with acetone (135 ml). The wet cake was dissolved in water (75 ml) and put on a rotary evaporator to remove any acetone present. The resulting solution was stirred with Amberlite LA-2 resin (37.5 ml) in dichloromethane (75 ml) containing formic acid (2.6 ml) for 20 minutes. The phases were separated, and the aqueous phase re-extracted with Amberlite LA-2 resin (37.5 ml) in dichloromethane (75 ml) containing formic acid (2.6 ml). The mixture was stirred for 20 minutes and separated. The aqueous phase was washed with dichloromethane (37.5 ml). The two phases were separated. The pH of the aqueous solution was lowered over 30 minutes to 2.8 by the addition of 50% v/v orthophosphoric acid. The resulting suspension was cooled to 0° and stirred for 90 minutes. The product was collected by vacuum filtration, washed with ice-cold water (2×30 ml) and dried overnight in vacuo at 40° to give the title compound (9.84 g). The U.V. spectrum resembled that of the product of Example 3.

EXAMPLE 5

(6R,7R)-7-(D-5-Benzamido-5-carboxypentanamido-3-(1-pyridiniummethyl)ceph-3-em-4-carboxylate A mixture of (6R,7R)-3-acetoxymethyl-7-(D-5-benzamido-5-carboxypentanamido)ceph-3-em-4-carboxylic acid (0.5 g), dichloromethane (25 ml), pyridine (0.24 ml) and trimethylchlorosilane (0.64 ml) was heated under reflux for 1 hour then cooled to ambient temperature. Trimethyliodosilane (0.85 ml) was added to the stirred clear solution and the flask was surrounded with aluminium foil. After one hour there was a yellow/brown suspension and a white precipitate. N,N-Dimethylformamide (5 ml), propylene oxide (1 ml) and pyridine (0.48 ml) were added in succession and the mixture was stirred for 30 minutes at ambient temperature. A 1 ml aliquot was removed and the dichloromethane evaporated in a stream of nitrogen. The residue was diluted to 10 ml with 0.05M ammonium dihydrogen phosphate in 10% v/v acetonitrile in water. An aliquot of this solution was applied to an h.p.l.c. column and elution was monitored photometrically at 260 nm. Several components were eluted; one had a retention time corresponding to that of an authentic specimen of the title compound. Thin-layer chromatographic examination (kieselgel, with development by acetonitrile:water:acetic acid in the proportions 60:20:0.4 by volume) revealed a mixture of components, one of which had an R$_f$ value (ca 0.2) identical to that of an anthentic specimen of the title compound and visualising the same purplish blue after exposure to a solution of potassium iodoplatinate.

EXAMPLE 6

(6R,7R)-7-amino-3-(1-pyridiniummethyl)ceph-3-em-4-carboxylic acid dihydrochloride dihydrate N,N-dimethylaniline (7.6 ml) was added with stirring to (6R,7R)-7-[D-5-benzamido-5-carboxypentanamido]-3-(1-pyridiniummethyl)ceph-3-em-4-carboxylate (5.38 g) and methylene chloride (50 ml). After 5 minutes trimethylchlorosilane (7.6 ml) was added and the mixture was stirred for 45 minutes at a temperature of 30°-32°. The resulting solution was cooled to −35° and phosphorus pentachloride (6.24 g) was added in one portion. The reaction mixture was stirred at −28° to −32° for 1 hour.

The iminochloride solution was cooled to −35° and added over 1.5 minutes to a pre-cooled (−20°), stirred solution of butan-1,3-diol (8 ml) and methylene chloride (20 ml). The flask which contained the iminochloride was rinsed with methylene chloride (5 ml) and added to the reaction mixture. The temperature had risen to −3° and a suspension was formed which was stirred for 30 minutes at 0°.

Water (7 ml) was added and after stirring the lower organic layer was separated and the aqueous phase collected. The organic layer was once again extracted with water (6 ml). The aqueous extracts were combined and cooled in an ice-bath for 30 minutes, when a thick crystalline mass was formed. This was stirred and diluted with isopropanol (50 ml) over 30 minutes. The resultant slurry was refrigerated for 1 hour.

The product was collected by filtration. The bed was sucked dry and displacement washed with isopropanol at 0° (2×20 ml).

The product was dried in vacuo at room temperature for 18 hours and then equilibrated at room temperature for several hours to yield crystalline title compound (3.6 g). $[\alpha]_D^{20} -57°$ (ca. 1%; 0.2M pH6 phosphate buffer), UV $E_{1cm}^{1\%}$ 316 at $\lambda$max 259 nm, 212 at $\lambda$inf 271.5 nm; water content (Karl Fischer) 9.7% m/m; h.p.l.c. purity 99.2%; chlorine content 17.4%.

I claim:

1. A process for the preparation of a 7-amino-cephalosporin compound of formula

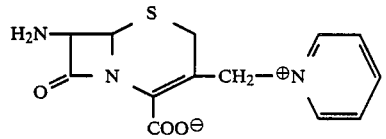

or a salt thereof, which comprises removing the 7-side chain from a compound of the formula

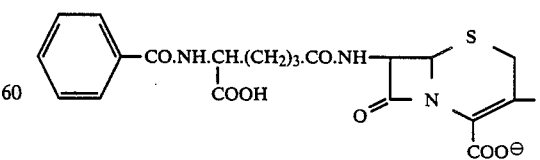

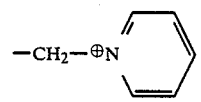

or a salt thereof to form said 7-amino-cephalosporin compound in high yield and purity.

2. In a process for the preparation of a 7-amino-cephalosporin compound of formula

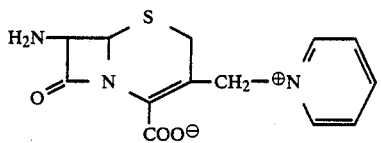

from Cephalosporin C or desacetyl Cephalosporin C by N-acylation of the 7-(aminoadipoyl) group and conversion of the 3-position substituent into a 3-pyridiniummethyl group to form a compound of formula

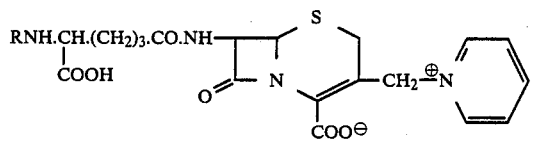

in which R is an acyl group, followed by removal of the 7-(acylaminoadipoyl) group, wherein the improvement comprises the N-benzoylation of the 7-aminoadipoyl) group to form a compound wherein R is benzoyl and the production of the 7-amino-cephalosporin compound in high yield and purity.

3. In a process for the preparation of a 7-acylamido-3-pyridiniummethyl cephalosporin from a compound of formula

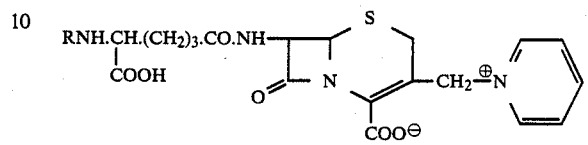

in which R represents an acyl group; or a salt thereof, wherein the R containing 7-(acylaminoadipoyl) group is removed from said compound to form a corresponding 7-amino compound which is acylated to form said 7-acylamido-3-pyridiniummethyl cephalosporin; wherein the improvement comprises removing a 7-(benzoylaminoadipoyl) group from a compound of said formula wherein R is a benzoyl group to obtain said 7-acylamino-3-pyridinium compound in high yield.

* * * * *